United States Patent
Ramamurti et al.

(10) Patent No.: US 6,635,072 B1
(45) Date of Patent: *Oct. 21, 2003

(54) SAFETY RATCHET MECHANISM

(75) Inventors: Balaji S. Ramamurti, West Chester, PA (US); Barclay Ross Davis, Downington, PA (US); G. Kris Kumar, West Chester, PA (US); Thomas J. Runco, Devon, PA (US); Thomas Steffen, Montreal (CA)

(73) Assignee: Synthes, Paoli, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 305 days.

(21) Appl. No.: 09/620,045

(22) Filed: Jul. 20, 2000

(65) Prior Publication Data (65)

(51) Int. Cl.⁷ .............................................. A61B 17/28
(52) U.S. Cl. ...................................................... 606/208
(58) Field of Search ................................ 606/208, 205, 606/88, 86; 81/15.9, 318, 336, 338

(56) References Cited

U.S. PATENT DOCUMENTS

| | | | | |
|---|---|---|---|---|
| 507,973 A | * 10/1893 | Cox | ................................ | 81/336 |
| 595,512 A | * 12/1897 | Anderson | ..................... | 81/318 |
| 920,536 A | * 5/1909 | Caldwell | ....................... | 81/318 |
| 1,158,345 A | * 10/1915 | Weaver | ......................... | 81/320 |
| 3,039,337 A | 6/1962 | Stuart-Prince | .................. | 81/15 |
| 3,470,872 A | 10/1969 | Grieshaber | .................... | 128/17 |
| 3,564,694 A | * 2/1971 | Millheiser | ..................... | 29/229 |
| 4,462,404 A | 7/1984 | Schwarz et al. | ............. | 128/321 |
| 4,538,485 A | * 9/1985 | Saila | .............................. | 81/320 |
| 4,602,535 A | 7/1986 | Wiener et al. | ................. | 81/313 |
| 4,896,661 A | 1/1990 | Bogert et al. | .................. | 606/86 |
| 4,961,742 A | * 10/1990 | Torre | ............................ | 606/147 |
| 5,174,300 A | 12/1992 | Bales et al. | ................... | 128/751 |
| 5,176,702 A | 1/1993 | Bales et al. | ................... | 606/208 |
| 5,250,050 A | * 10/1993 | Poggie et al. | .................. | 606/79 |
| 5,293,878 A | * 3/1994 | Bales et al. | ................... | 600/564 |
| 5,297,538 A | 3/1994 | Daniel | ........................... | 128/20 |
| 5,344,061 A | 9/1994 | Crainich | ...................... | 227/182 |
| 5,417,701 A | 5/1995 | Holmes | ......................... | 606/148 |
| 5,674,244 A | * 10/1997 | Mathys | ......................... | 606/208 |
| 5,697,933 A | * 12/1997 | Gundlapalli et al. | ......... | 606/206 |
| 6,159,217 A | * 12/2000 | Robie et al. | ................. | 606/207 |

FOREIGN PATENT DOCUMENTS

FR         1347337 A        1/1963

* cited by examiner

Primary Examiner—David O. Reip
Assistant Examiner—Victor Nguyen
(74) Attorney, Agent, or Firm—Pennie & Edmonds LLP (57) ABSTRACT

A hand tool having first and second handle portions and a toothed bar that has first and second terminal ends, a plurality of teeth having free ends, and at least one shield member adjacent the teeth and having at least a portion which extends beyond the free ends of the teeth, wherein the toothed bar is pivotally attached at its first terminal end to a first handle portion and the teeth of the toothed bar engage with a pawl associated with the second handle. The invention is also directed to a safety ratchet mechanism for preventing undesired relative movement of two handle portions of a hand tool, wherein the toothed bar has a first end that is pivotally connected to at least one handle portion and a second end adapted and configured to move relative to the second handle portion when the handle portions undergo relative movement, and wherein the toothed bar has a plurality of teeth that are designed to interact with a pawl. The toothed bar may further have two shield members with the teeth extending therebetween to further shield the operator's hands or gloves from the teeth. The second handle portion may have an opening through which the toothed bar can slide, and a catch may be mounted on the toothed bar to prevent it from sliding out of the opening, and a stop may be associated with the handle to prevent the second end from being disassociated with the handle portion.

37 Claims, 9 Drawing Sheets

SAFETY RATCHET MECHANISM

FIELD OF THE INVENTION

The present invention relates to a ratchet mechanism for a hand tool and, in particular, to a ratchet mechanism for locking the jaws of a hand tool such, as for example, a surgical forceps, in a desirable position.

BACKGROUND OF THE INVENTION

Pliers-shaped tools generally have jaws positioned by movable plural handles. A typical pliers-shaped tool has two lever arms that intersect at a pivot point so that the two ends of the arms form first and second handles that an operator can separate or close. For certain uses, it is desirable for the operator to be able to lock the handles of a pliers-shaped tool in a desired position, which may be open, closed, or somewhere between those two extremes. For example, it is desirable during a surgical procedure for an instrument to clamp an object with the jaws remaining in position without the user having to apply a force to the handles. Various known locking mechanisms are used to lock the handles of pliers-shaped tools.

Pliers-shaped surgical instruments such as forceps use a locking mechanism to obtain a graduated closing of the forceps. In this manner, the jaws of the device may be locked in a closed, open or in between position, and a graduated closing of the forceps may be obtained. One type of locking mechanism used with forceps is a ratchet mechanism comprising a toothed member, one end of which is connected to one end of a first forceps handle. A longitudinal edge of the bar has a set of angled teeth that are engageable with the end of the second forceps handle. The end of the toothed member, that is remote from the hinge is unattached, but the bar is urged toward the forceps handles by a spring, causing contact between the teeth and the second forceps handle. To lock the forceps jaws in a closed position, the operator must squeeze the handles until the end of the second forceps handle engages the teeth of the toothed bar at the desired position. To unlock the forceps, the handles of the forceps are squeezed together slightly to release the engagement between the second forceps handle and the teeth, and the ratchet bar is lifted off the teeth with manual pressure. This locking mechanism suffers from the disadvantage that the unattached second end of the toothed member is not contained by the second handle such that it can move out of position so that it does not engage and lock with the second handle. The unattached and unconstrained second end often requires the operator to use two hands to operate the instrument. The locking mechanism further suffers from the disadvantage that the angled teeth can cut and nick the operator's hand, a particular disadvantage during a surgical procedure where the gloves of the surgeon could be torn and the surgeon's hands cut.

Another pliers-shaped tool having a locking mechanism is disclosed in U.S. Pat. No. 5,297,538, which describes a surgical retractor/compressor two removable, serrated locking mechanisms that are used to lock the arms of the pliers-shaped device in either a retraction or a compression mode. In this type of device, one locking mechanism at a time is removably attached to the surgical instrument. One locking mechanism has serrations that are angled in one direction. The other locking mechanism has serrations that are angled in the opposite direction. When a locking mechanism is attached to the surgical instrument, one end of the locking mechanism clips onto one handle, and the serrations in the locking mechanism engage with one of two oppositely angled sets of serrations that are formed on the second handle of the instrument, thereby locking the handles in either a retraction or a compression mode. Releasing or unlocking the handles typically requires the user to use both hands to hold the instrument handles and pull the locking mechanism to release it from the serrations. To do so, the user must apply a force transverse to that which is normally exerted when gripping a pliers-shaped tool. This instrument also suffers the drawback of having angled teeth and serrations which can scratch, cut and nick an operator's hands or gloves.

Yet another locking mechanism for a pliers-shaped tool is disclosed in U.S. Pat. No. 4,896,661, which describes a multi-purpose orthopedic ratcheting forceps having interchangeable tip elements and a reversible ratchet mechanism for controlling the tip elements or jaw portions. The ratchet mechanism of that invention has a multi-position pawl mechanism on a first arm of the tool. A curved ratchet toothed member is secured in a channel of the second tool arm. The toothed member extends toward the first arm and passes through the pawl mechanism, where a movable pawl is engageable with the toothed member. The operator must move the pawl mechanism to engage and disengage the teeth of the ratchet from the pawl. When the pawl is moved to a first position, the arms of the forceps device pivot to ratchet open the jaw portions. When the pawl is moved to a second position, it allows the arms to ratchet closed the jaws. In the third position, the pawl is disengaged from the ratchet toothed member. Thus, the operator must re-position the pawl mechanism to cause both engagement and disengagement of the pawl. Furthermore, the sharp teeth of the curved ratchet member are in close proximity with, and point toward, the hand grip of the forceps device, thus posing a risk of catching or nicking the operator's glove or hand.

It is desirable to provide a locking mechanism for a pliers-shaped tool whereby a controlled closing or opening of the tool jaws can be achieved with a mechanism that minimizes the risk of catching or nicking the hands or gloves of an operator, and wherein the tool handles and jaws can be adjusted or repositioned in a simple, easy to use manner with one hand. It is also desirable to provide a locking mechanism that limits the opening of the tool handles and facilitates one-handed use for all applications of the tool.

SUMMARY OF THE INVENTION

It is an object of one or more embodiments of the present invention to provide a locking mechanism for a pliers-shaped tool whereby a controlled closing or opening of the tool jaws can be achieved with a mechanism that minimizes the risk of catching or nicking the hands or gloves of an operator, and wherein the tool handles and jaws can be adjusted or repositioned in a simple, easy to use manner with one hand. It is a further object of one or more embodiments to provide a locking mechanism that limits the opening of the tool handles and facilitates one-handed use for all applications of the tool.

In one embodiment, the present invention is directed to a hand tool that has first and second handle portions, the second handle portion having a pawl associated therewith, and a ratchet bar having first and second terminal ends. The toothed bar or ratchet bar has a plurality of teeth, each one of which has a free end. The toothed bar may further include at least one shield member adjacent the teeth and having at least a portion extending beyond the free ends of the teeth. The toothed bar is preferably pivotally attached at its first terminal end to the first handle portion and the teeth of the toothed bar engage the pawl associated with the second handle portion. The first handle portion of the hand tool may include a biasing spring adapted and configured to pivot the toothed bar into engagement with the pawl. The biasing spring may comprise a leaf spring mounted to the first handle portion. The second handle portion may have an opening through which the toothed bar slides. The toothed bar may have a catch to prevent it from becoming disassociated from the second handle, by for example, sliding out of the opening. The second handle portion may also have a stop to prevent the toothed bar from pivoting away from the pawl.

In a further embodiment, the invention is directed to a ratchet mechanism for preventing undesired relative movement of two handle portions of a hand tool, including a toothed bar that has a first end which may be adapted and configured to be pivotally connected to at least one handle portion and a second end which may be adapted and configured to move relative to the other handle portion when the handle portions undergo relative movement. The toothed bar has a plurality of teeth designed and configured to interact with a pawl on the hand tool, the teeth further having free ends, and the toothed bar may include at least one shield member having at least a portion which extends beyond the free ends of the teeth. An opening may be formed in the other handle, and the toothed bar slides through the opening. The first end of the toothed bar may be designed and configured to receive a biasing force to pivot the toothed bar into engagement with the pawl. Furthermore, the first end of the toothed bar may be designed and configured to interact with a free end of a leaf spring mounted to the handle portion of the hand tool.

The hand tool and/or the ratchet mechanism may have a catch on the toothed bar to prevent the toothed bar from sliding completely through the opening. In one embodiment, two shield members are located adjacent the teeth of the toothed bar. Alternately, the toothed bar has two rows of teeth and at least one shield member located between the two rows of teeth. When the toothed bar has two rows of teeth the pawl may have a slot. The two rows of teeth may have two exposed lateral edges that are rounded and/or tapered toward the shield member.

The toothed bar may be manufactured in any number of ways including for example machining and/or casting, and may be made from any number of materials. The toothed bar further may be designed and configured to prevent the handle portions of the tool from separating unless an operator disengages the teeth from the pawl. The teeth may be arranged as sawtooth serrations.

In a further embodiment, the invention is a hand held tool having a first extending member; a second extending member having an opening associated therewith and a pawl. The hand held tool also has a working end movable by relative movement of the extending members, and a toothed bar having a first end pivotally connected to the first extending member and a second end adapted and configured to move through the opening in the second extending member. The toothed bar has teeth to engage the pawl to prevent undesirable relative movement of the first and second extending members.

Furthermore, the first and second extending members may be moved relative to each other in both directions by use of one hand of the operator. The toothed bar of the hand held tool may have a longitudinal axis between the first end and the second end, and the teeth and pawl may be configured to have contact surfaces that are substantially perpendicular to the longitudinal axis of the toothed bar. The toothed bar may also be curved.

The first and second extending members of the hand held tool may be designed and configured to prevent the toothed bar from being disassociated from the second extending member. In one embodiment, a stop may further prevent the toothed bar from pivoting away from the second extending member.

Furthermore, the hand held tool may be provided with a catch on the toothed bar to prevent the toothed bar from sliding through the opening. The opening may have a U-shape having an open back.

The hand held tool may also have a biasing member to urge the teeth into engagement with the pawl. The biasing member that urges the teeth into engagement with the pawl may be a leaf spring associated with the first extending member. The leaf spring biases the toothed bar to rotate about a pivotal connection on the hand held tool. The biasing member may alternatively engage the toothed bar and the second extending member.

The hand tool may be a surgical instrument, and the ratchet mechanism may be designed and adapted for use with a surgical instrument.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
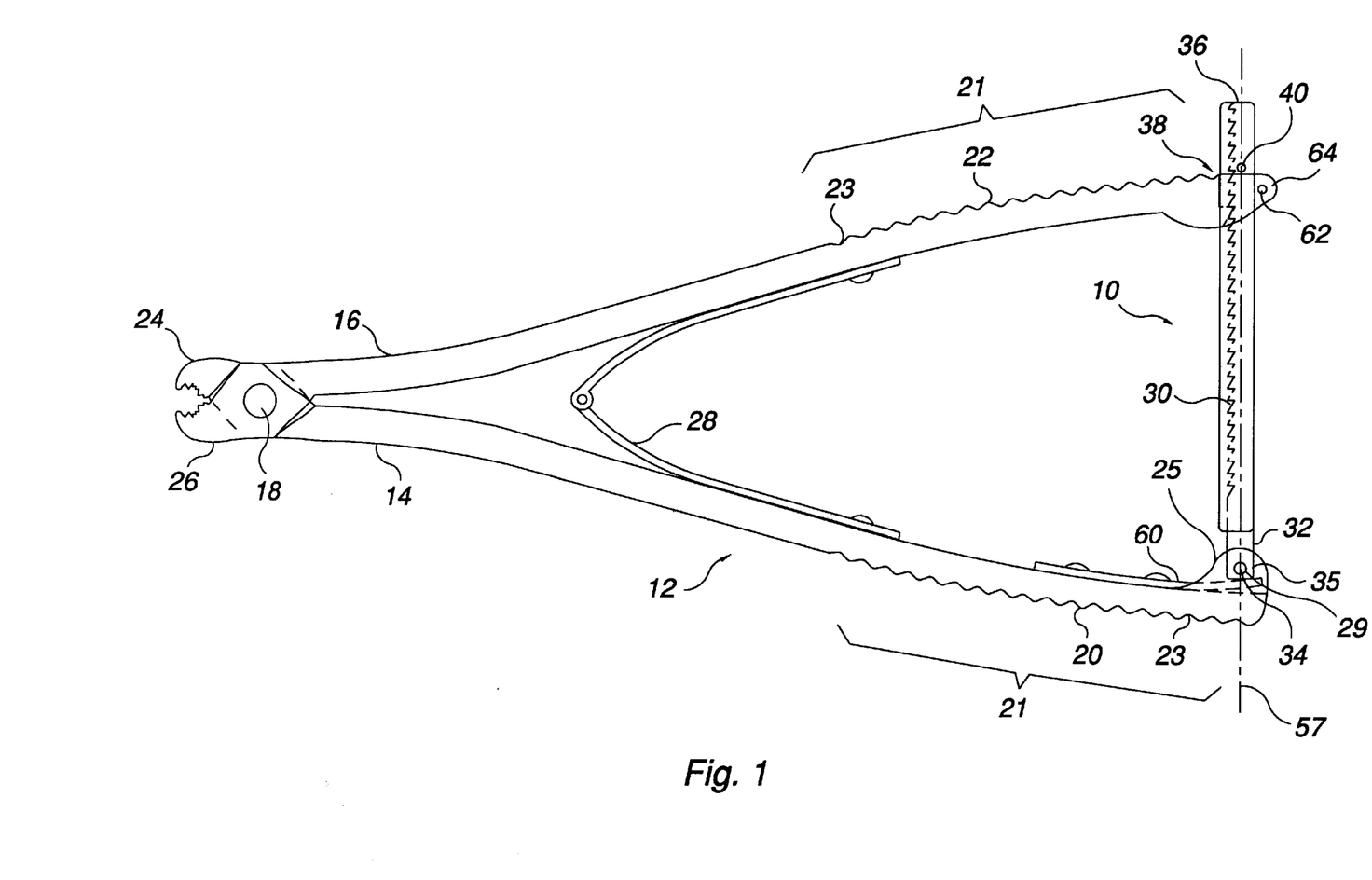
FIG. 1 is a partially broken away side elevational view illustrating a preferred embodiment of the ratchet mechanism of the invention on a pliers-shaped tool.

FIG. 1 illustrates a standard pliers-shaped tool with a ratchet mechanism 10 according to a preferred embodiment of the invention. For purposes of the present discussion, the pliers-shaped tool 12 is described as having two lever arms 14 and 16 which intersect at and rotate or pivot about a pivot point 18. Two ends of the arms form handles 20 and 22 which an operator can separate or squeeze together. The other two ends form jaws 24, 26 or working ends which are opened and closed in response to movement of handles 20, 22. Handles 20, 22 may have grips 21 formed or placed thereon to assist in gripping the handles. One form of grips, illustrated in FIG. 1, are grooves 23 formed in the handle along its length. Tool 12 may further have a spring 28 or other mechanism for urging handles 20 and 22 toward or away from each other. In general, the tool upon which the ratchet mechanism is mounted has two elongate handles and has jaws that move together or apart when the handles are squeezed together. The movement of the jaws may be scissors-like, vise-like or otherwise. Tools such as those generally described above are exemplified in, for example, U.S. Pat. Nos. 5,297,538; 5,176,702; 4,602,535; 3,470,872; 3,039,337; and 1,158,345. Other configurations are contemplated as being within the scope of the invention and will be evident to those of ordinary skill in the field.

As used in the present discussion, the term "distal" or the like refers to the end or direction toward the jaws of the pliers-shaped tool. Conversely, the term "proximal" or the like refers to the end or direction that is located or positioned furthest from the jaws, i.e., the ends toward the handles.

FIG. 1 illustrates an embodiment of the safety ratchet mechanism 10 of the present invention, which includes a toothed bar 30 having one end 32 that is pivotally connected to a handle 20 of the pliers-shaped tool at pivot point 34. In this embodiment, handle 20 has knuckles 25, 27 (not shown) having holes 29, 31 (not shown), respectively, formed therein. End 32 of the toothed bar is formed with an aperture 33, shown in FIG. 2. End 32 is positioned between knuckles 25, 27, and aperture 33 is aligned with holes 29, 31. A rod 35 is inserted through holes 29, 31 and aperture 33 to attach the toothed bar 30 to handle 20. Preferably, rod 35 is designed so that it cannot be removed by a user during use of the tool. Other manners of attaching toothed bar 30 to handle 20 are contemplated as being within the scope of the invention and will be evident to those of ordinary skill in this field.

Preferably, the opposite end 36 of bar 30 extends toward second handle 22 and through an opening 38 also in second handle 22 of the tool. Opening 38 may also be adjacent to the handle such as along its side or at the end of the handle. Opening 38 contains bar 30 and is sized to allow bar 30 to slide therethrough. To prevent toothed bar 30 from sliding out of opening 38 when the handles are spread apart, bar 30 is preferably provided with a catch 40 near end 36. Preferably, the catch 40 is formed as a pin 39 extending crosswise through bar 30 near end 36. Catch 40 has a length that is greater than the width of opening 38. Thus, catch 40 prevents bar 30 from sliding out by abutting against handle 22 when handles 20 and 22 are spread apart. Catch 40 prevents excessive opening of the jaws and/or handles of the tool. The catch 40 described herein should not be viewed as limiting the invention since other ways of preventing withdrawal of the toothed bar from an opening may be incorporated, such as, for example, an end member 41 (shown in FIG. 7).

Figure 2:
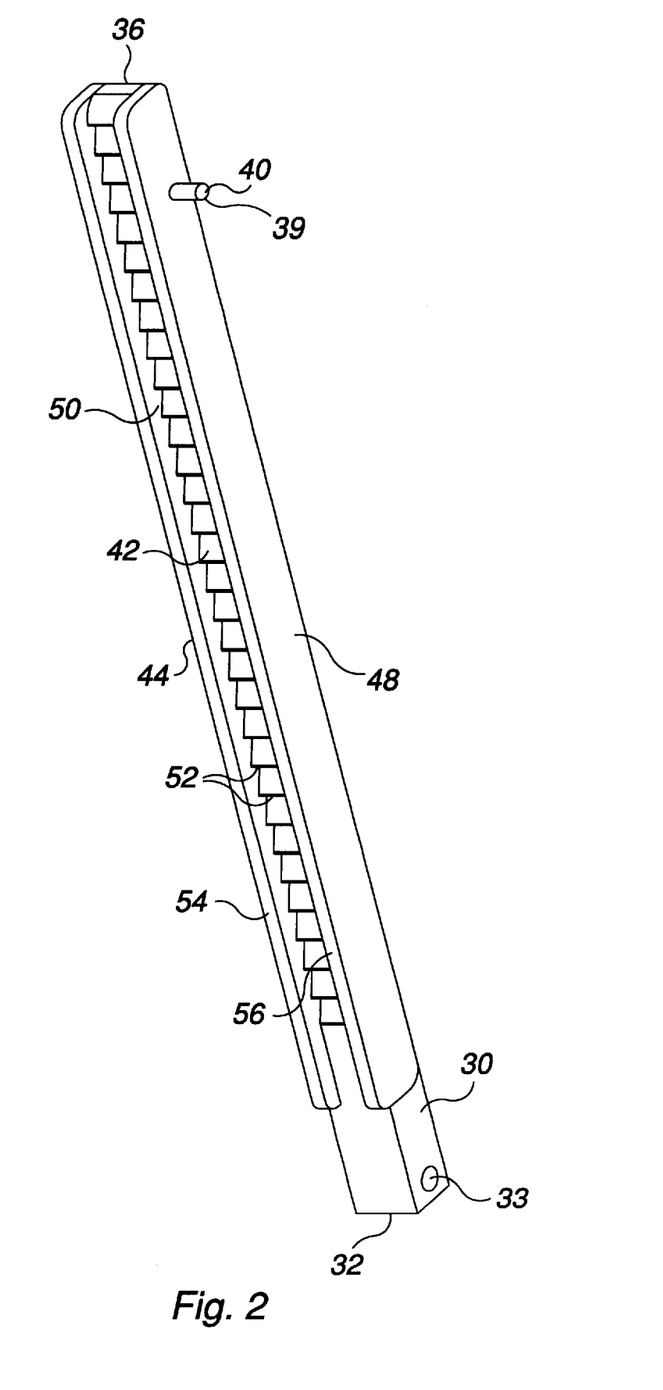
FIG. 2 is a perspective view of the toothed bar of FIG. 1.
Figure 3:
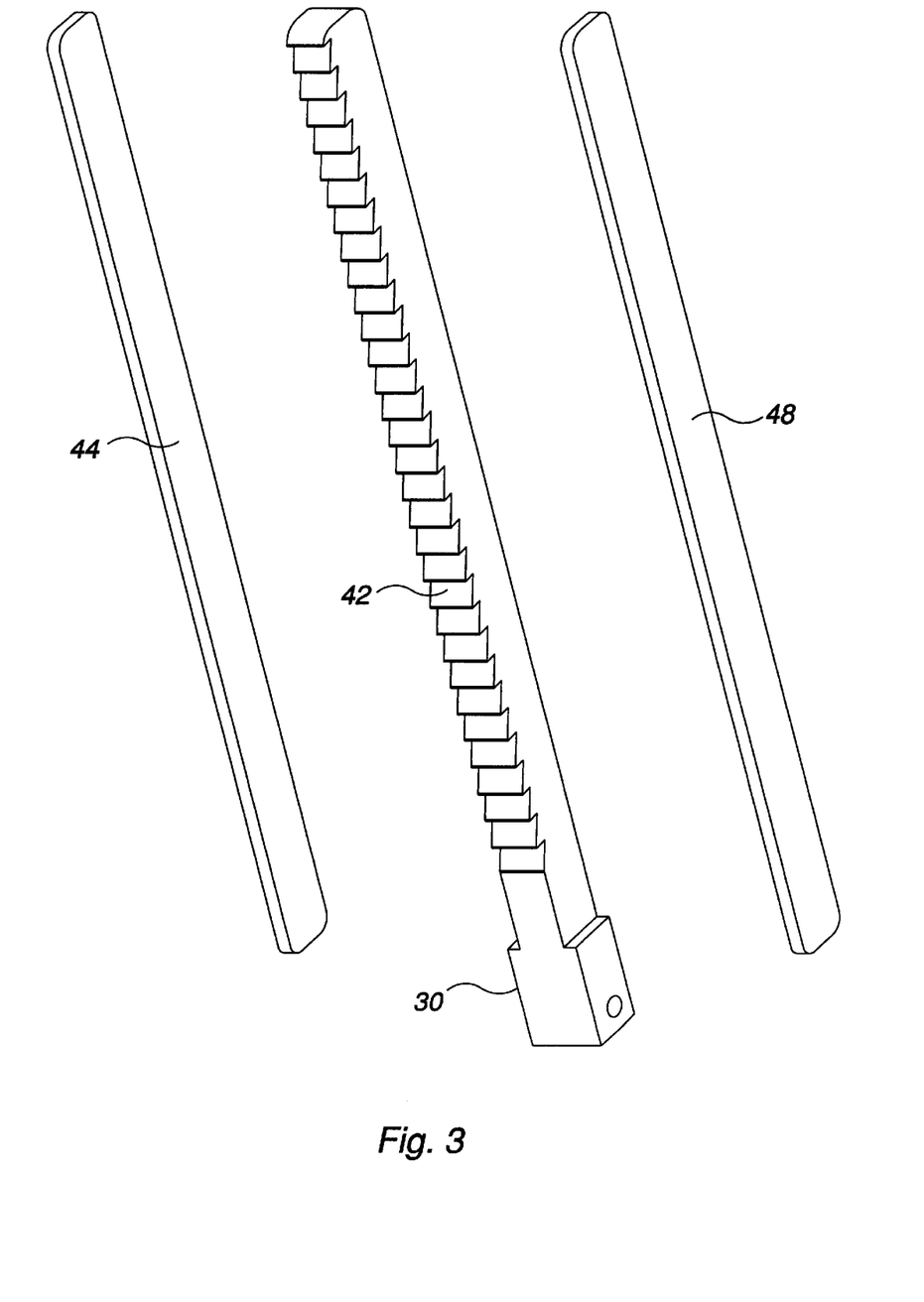
FIG. 3 is an exploded view of a toothed bar having two shields.

In one embodiment of the invention, bar 30 has one row of teeth 42 flanked by shields 44 and 48, illustrated in FIG. 2 and in FIG. 3. Teeth 42 are recessed in a channel 50 formed by shields 44 and 48 such that the free ends or edges 52 of teeth 42 are recessed below the edges 54 and 56 of shields 44 and 48, respectively. The teeth 42 of ratchet mechanism 10 engage a fixed pawl 58 that is formed on handle 22 and that extends into opening 38 in handle 22. Pawl 58 is illustrated in a partial cut-away side view of handle 22 in FIG. 4 and in a partial plan view of handle 22 in FIG. 5. Preferably, fixed pawl 58 extends proximally into the opening 38 through which the toothed bar 30 moves, and teeth 42 point distally toward the pawl. Teeth 42 engage the fixed pawl 58 to lock the tool in a desired position against the recoil of a mechanism such as spring 28 which biases the handles of the tool either together or apart. The shields 44 and 48 straddle the pawl 58 without interfering with the ratcheting function of the teeth and pawl.

Figures 4, 5, 6:
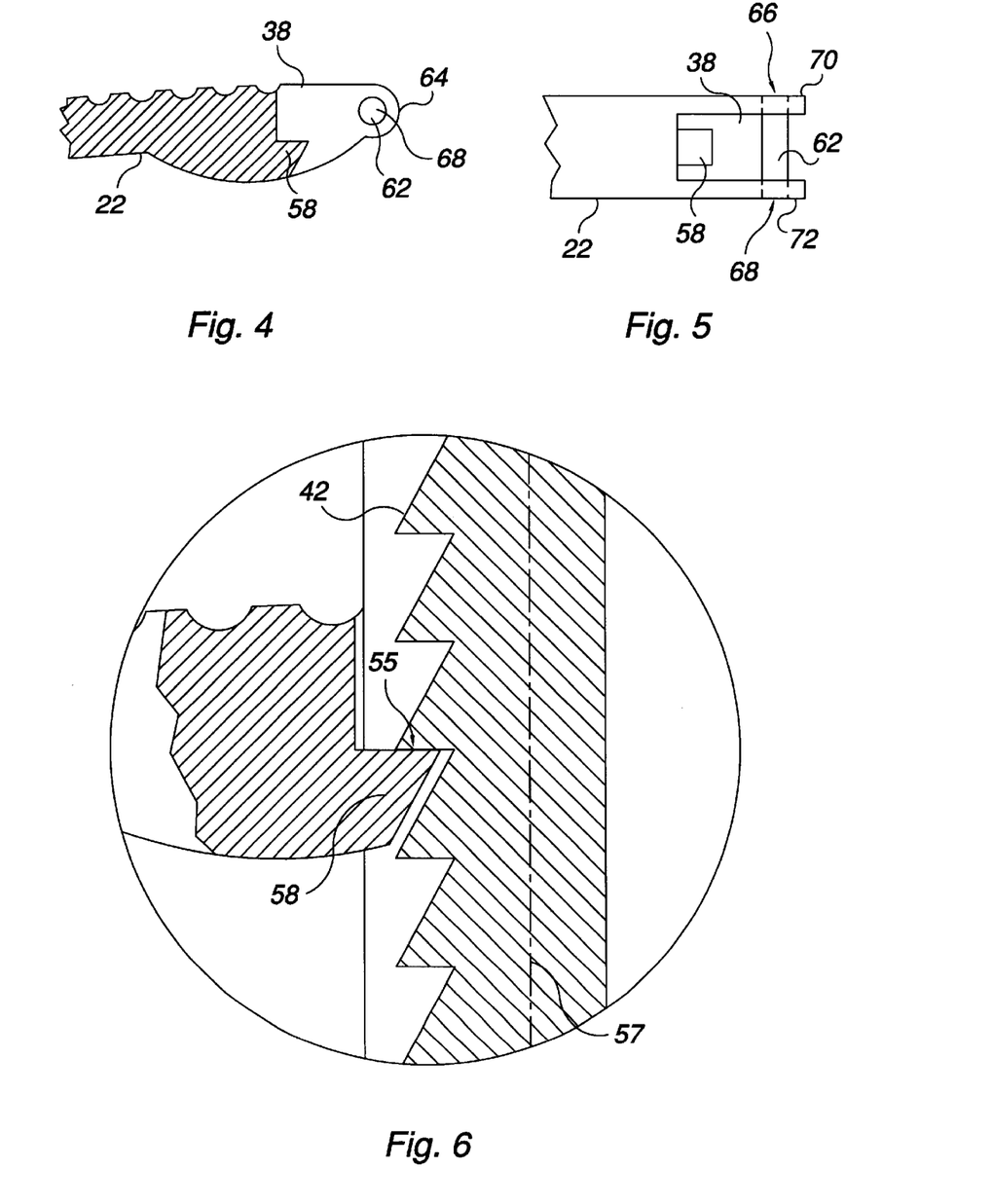
FIG. 4 is a cut-away detail showing the fixed pawl of the ratchet mechanism of FIG. 1.
FIG. 5 is a partial top plan view of the pawl and the tool handle opening through which the toothed bar of FIG. 1 slides.
FIG. 6 is a cross-sectional detail showing contact between the pawl and the teeth of the toothed bar.

The teeth and fixed pawl of the ratchet mechanism may have any geometry that serves to perform the ratcheting function, i.e., the shapes of the teeth and pawl must be such that the teeth are able to slide or ratchet past the pawl in one direction typically when the tool handles are simply squeezed together, but not in the other direction without applying a force to disengage the teeth. In other words, the surfaces of the pawl and teeth slide past one another in one direction but catch and lock when moved in the other direction. Preferably, the teeth and pawl have corresponding sawtooth serrations or profiles, as illustrated in FIGS. 2, 3, 4 and 6. When a tooth having a sawtooth profile engages a sawtooth-shaped pawl and the tool handles are locked, the contact surfaces 55 between the tooth and the pawl are perpendicular to the longitudinal axis 57 of the toothed bar 30, as illustrated in FIG. 6. When the contact surfaces are substantially perpendicular to the longitudinal axis 57, the pawl and ratchet can be disengaged without the operator squeezing the handles 20, 22 together to unlock the surfaces. The sloped portions of the sawtooth profiles enable the surfaces of the pawl and the teeth to slide over each other in a manner typical of ratchets. Thus, the graduated opening and closing of the jaws and/or handles of the tool are obtained.

The size and depth of the pawl and tooth profiles affect the step size of the graduated movement, and thus by controlling the length of the teeth along the longitudinal axis the step size of the graduated movement can be controlled. Further, in this manner, the size of the teeth along the length of the bar can be varied to control the step size. For example, the length of the teeth at one end of the bar can be made large while they are made small at the other end so that fine graduated movement can be utilized as the jaws approach the closed position.

A biasing spring 60 exerts a force against the pivotable end 32 of bar 30, thereby biasing bar 30 so that teeth 42 engage fixed pawl 58. Biasing spring 60 is exemplified in FIG. 1 by a curved leaf spring which is attached to tool handle 20 and which presses against pivotable end 32 of toothed bar 30. Although a leaf spring has been shown, it will be evident to those of ordinary skill in this field that other configurations can be used to bias the teeth 42 against fixed pawl 58. In addition, biasing spring 60 may be configured as an extension of tool spring 28 rather than as a separate element as illustrated in FIG. 1. Alternatively, biasing spring 60 may be positioned on tool handle 22 to urge the teeth 42 of bar 30 toward fixed pawl 58.

Because toothed bar 30 is biased toward fixed pawl 58, an external force such as that exerted by an operator's fingers is needed to disengage teeth 42 from pawl 58. When the toothed bar is disengaged in this manner, it may be preferable to limit the range of motion of the end 36 of the bar. Accordingly, a preferred embodiment of the ratchet mechanism of this invention provides a stop 62 on handle 22 to prevent the end 36 of toothed bar 30 from being pushed more than a short distance away from pawl 58. Stop 62 is located a sufficient distance away from fixed pawl 58 to ensure that teeth 42 can be disengaged from the pawl throughout the range of travel of handles 20 and 22. Additionally, the movement of the bar 30 is restricted by catch 40, which prevents the tool handles from separating more than a predetermined distance, which is limited by the length of the toothed bar and the position of catch 40 on the bar. Catch 40 and stop 62 limit the range of motion of the toothed bar and the tool handles and assist in permitting one-handed use of the tool. Unlike some prior ratchet tool mechanisms, the second end of the tool bar 30 remains associated with the handle and in an operable position.

Although stop 62 is illustrated in FIGS. 1, 4 and 5 as a pin, this embodiment should not be viewed as a limiting example. Opening 38, for instance, is illustrated in FIG. 5 as a U-shaped opening at the proximal end 64 of handle 22, wherein pin 62 is inserted through holes 66, 68 formed in extended members 70, 72, respectively, to close up the open proximal end of the U-shaped opening and retain toothed bar 30 in association with handle 22 (see FIG. 5). Alternatively, opening 38 may be a cut-out through-opening in handle 22, wherein the proximal edge of the through-opening forms a stop for limiting the travel of toothed bar 30 in the proximal direction.

Another embodiment of the ratchet mechanism of the invention omits opening 38 altogether. In this embodiment, the pawl extends in a proximal direction from the proximal end of one tool handle, and end 36 of the toothed bar 30 is unconstrained except for the biasing force urging it distally toward the pawl. Stop 62 and catch 40 are not used in this embodiment, and the end 36 of the toothed bar 30 may be disengaged entirely from the tool handle which has the pawl.

Also, although the ratchet mechanism illustrated in FIG. 1 is depicted at the proximal ends of tool handles 20 and 22, it is within the scope of the invention to locate the ratchet mechanism at a more distal location, i.e., preferably at some point between the proximal ends of the tool handles and the pivot point 18. Additionally, the teeth of the toothed bar are not required to point in the distal direction. The bar may be oriented such that the teeth point in the proximal direction, and the pawl points distally toward them. Alternatively, the teeth and pawl may be oriented in some direction other than distal and proximal. Furthermore, the overall shape of the toothed bar is not required to be rectilinear, as illustrated, but may be curvilinear with, for example, teeth extending outward from a curved portion of the bar and with curved shields extending farther outward than the free ends or edges of the teeth.

Figure 7:
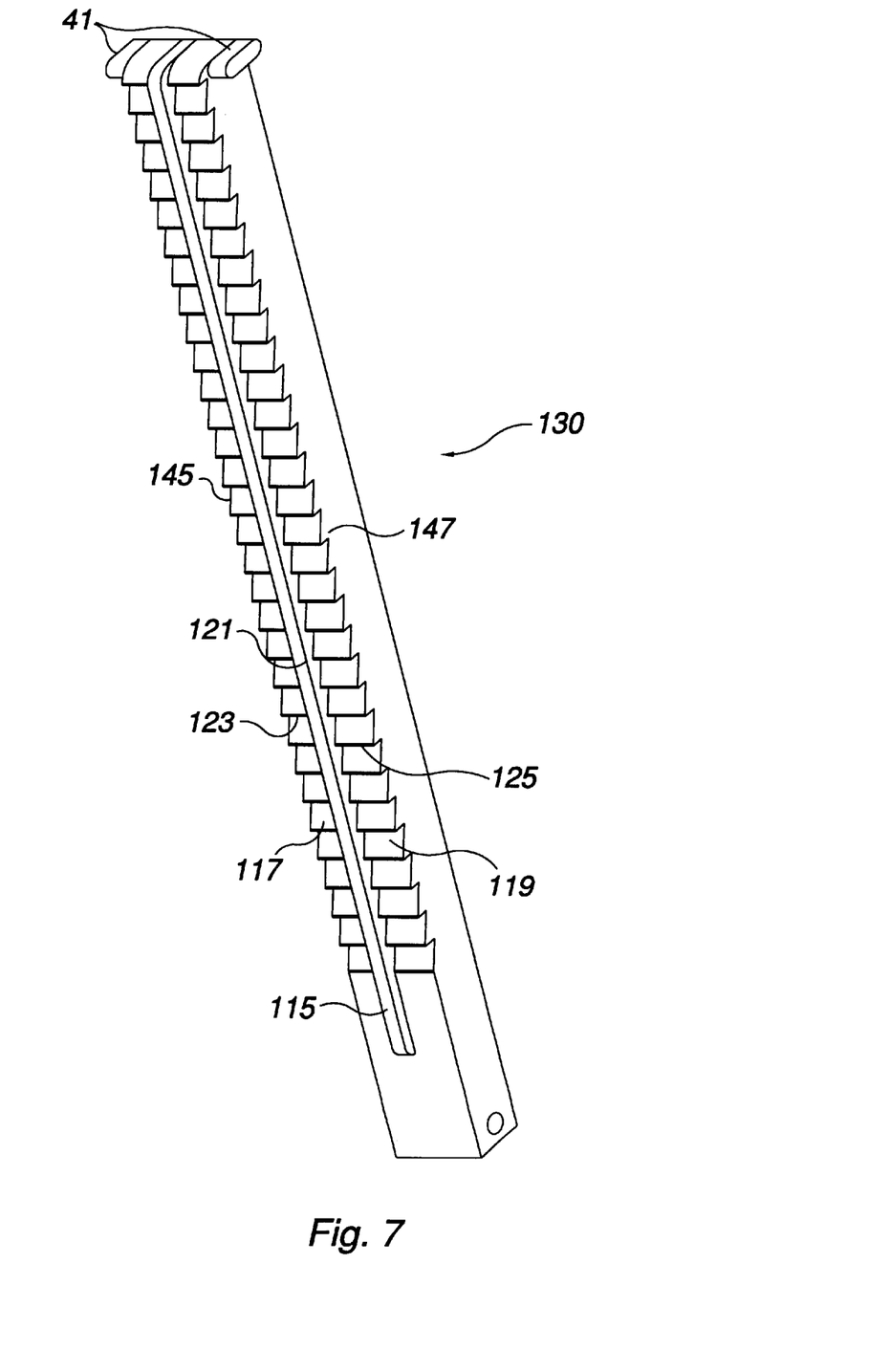
FIG. 7 is a perspective view of an embodiment of a toothed bar that has one shield.
Figure 8:
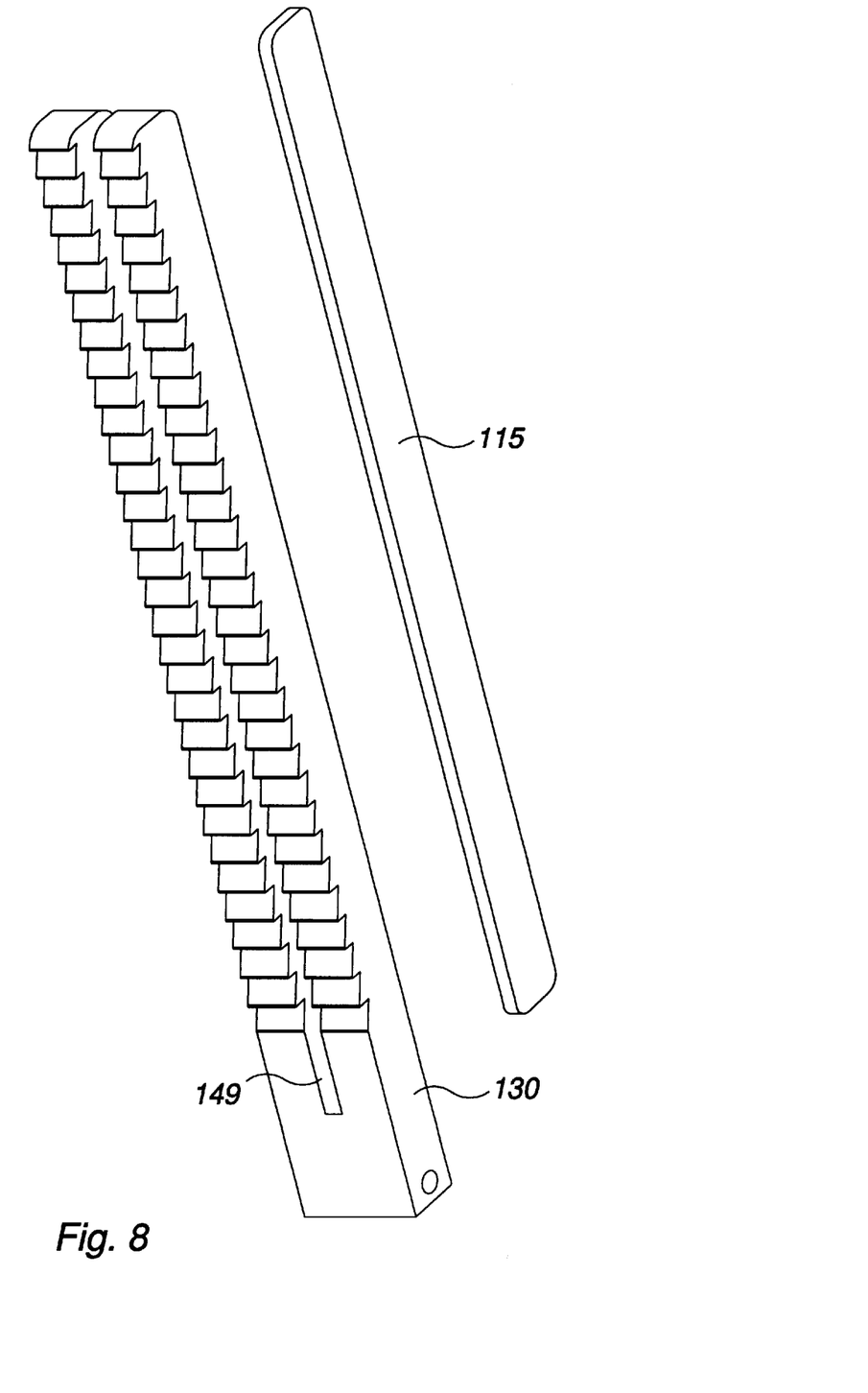
FIG. 8 is an exploded view of a toothed bar having one shield.
Figure 9:
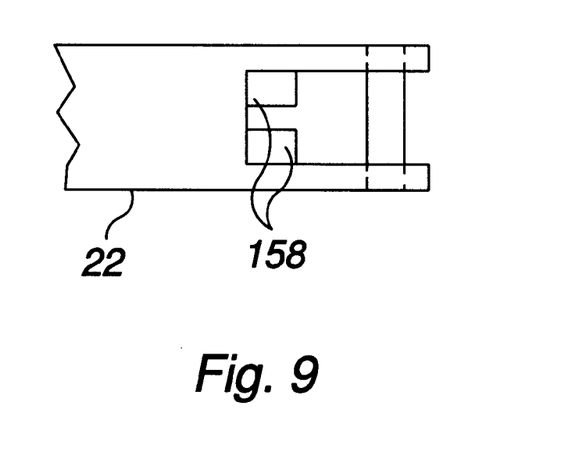
FIG. 9 is a partial top plan view of the tool handle opening showing a slotted pawl that engages the toothed bar of FIG. 6.
Figure 10:
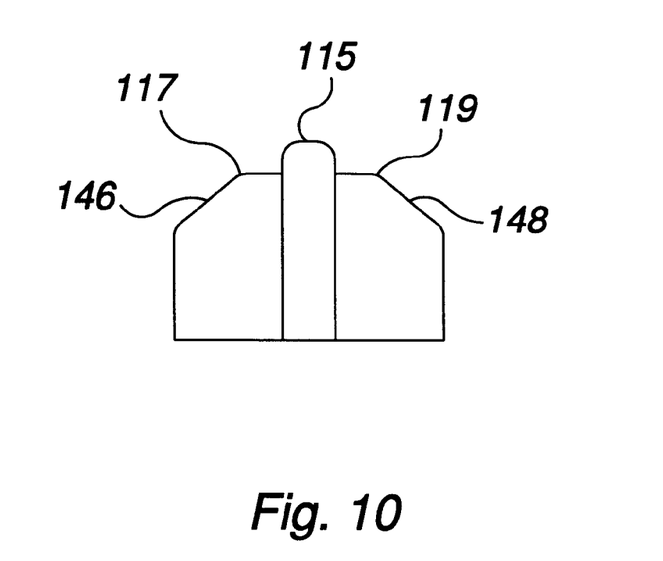
FIG. 10 is a cross-sectional detail of a toothed bar having one shield, showing tapered teeth.

In another embodiment of the invention, the ratchet mechanism comprises bar 130 with one shield 115 extending longitudinally between two sets of teeth 117 and 119, as illustrated in FIG. 7 and in FIG. 8. Shield 115 has an edge 121 that extends laterally outward from bar 130 beyond edges 123 and 125 of sets of teeth 117 and 119, respectively. For this embodiment, the pawl 158 is formed with a slot through its middle portion to allow shield 115 to slide through without interfering with the ratcheting function of the pawl and teeth, as illustrated in the partial top plan view of FIG. 9. Alternatively, the pawl may be formed of two prongs that are appropriately spaced apart for engaging teeth 117 and 119 without interfering with shield 115. Preferably, the exposed sides 145 and 147 of the teeth are rounded and/or tapered at lateral sides 146, 148 toward shield 115 to prevent an operator's hands or gloves from coming into contact with any sharp corners of the teeth which could cut the operator's hands or gloves, as illustrated in a cross-sectional view of toothed bar 130 in FIG. 10. In all other respects, this embodiment is substantially as described hereinabove.

Figure 11:
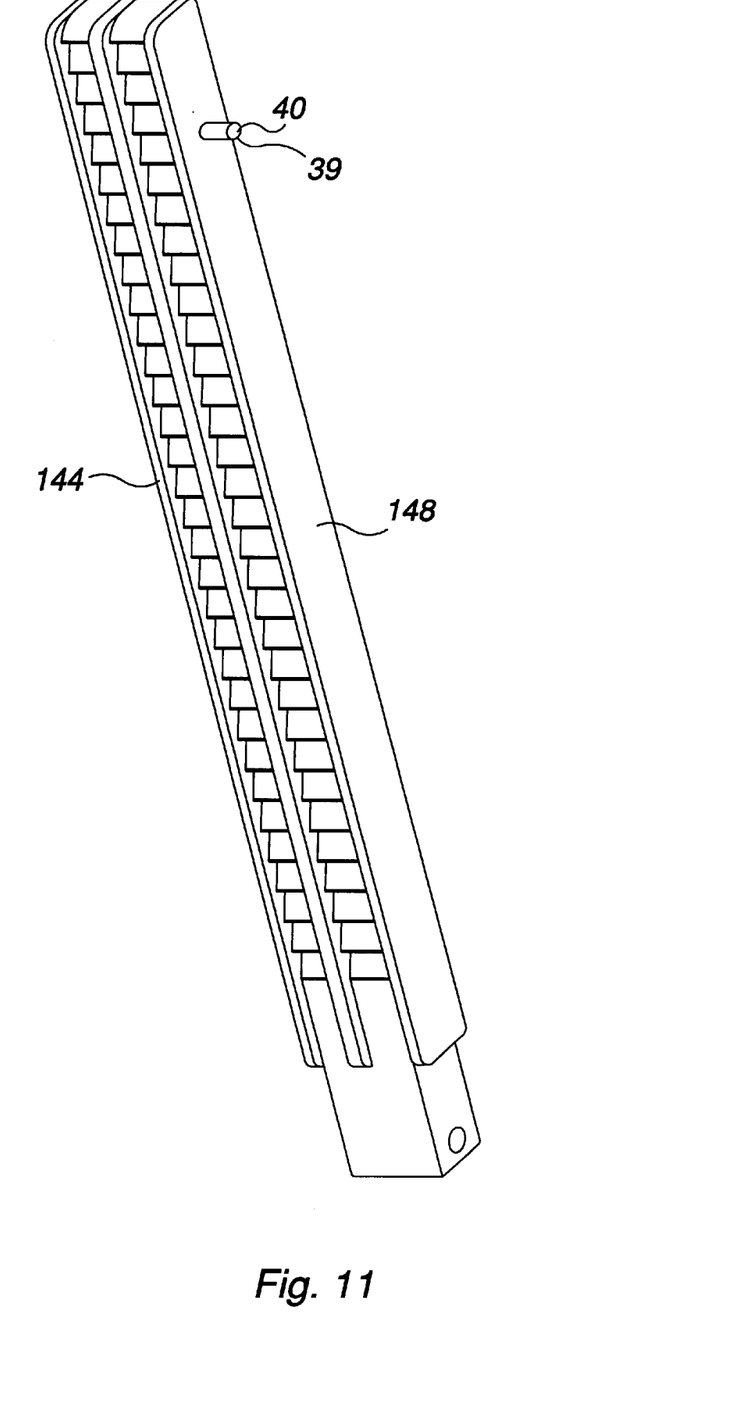
FIG. 11 is a perspective view of an embodiment of a toothed bar that has three shields.

Yet another embodiment of the invention has a toothed bar with two sets of teeth with a shield extending therebetween, and two more shields 144 and 148 on the outer flanks of the two sets of teeth, as illustrated in FIG. 11. For this embodiment, the pawl is suitably slotted, notched, or formed with prongs to engage the two rows of teeth to allow the shields to slide through without interfering with the ratcheting function of the pawl and teeth.

Figure 12:
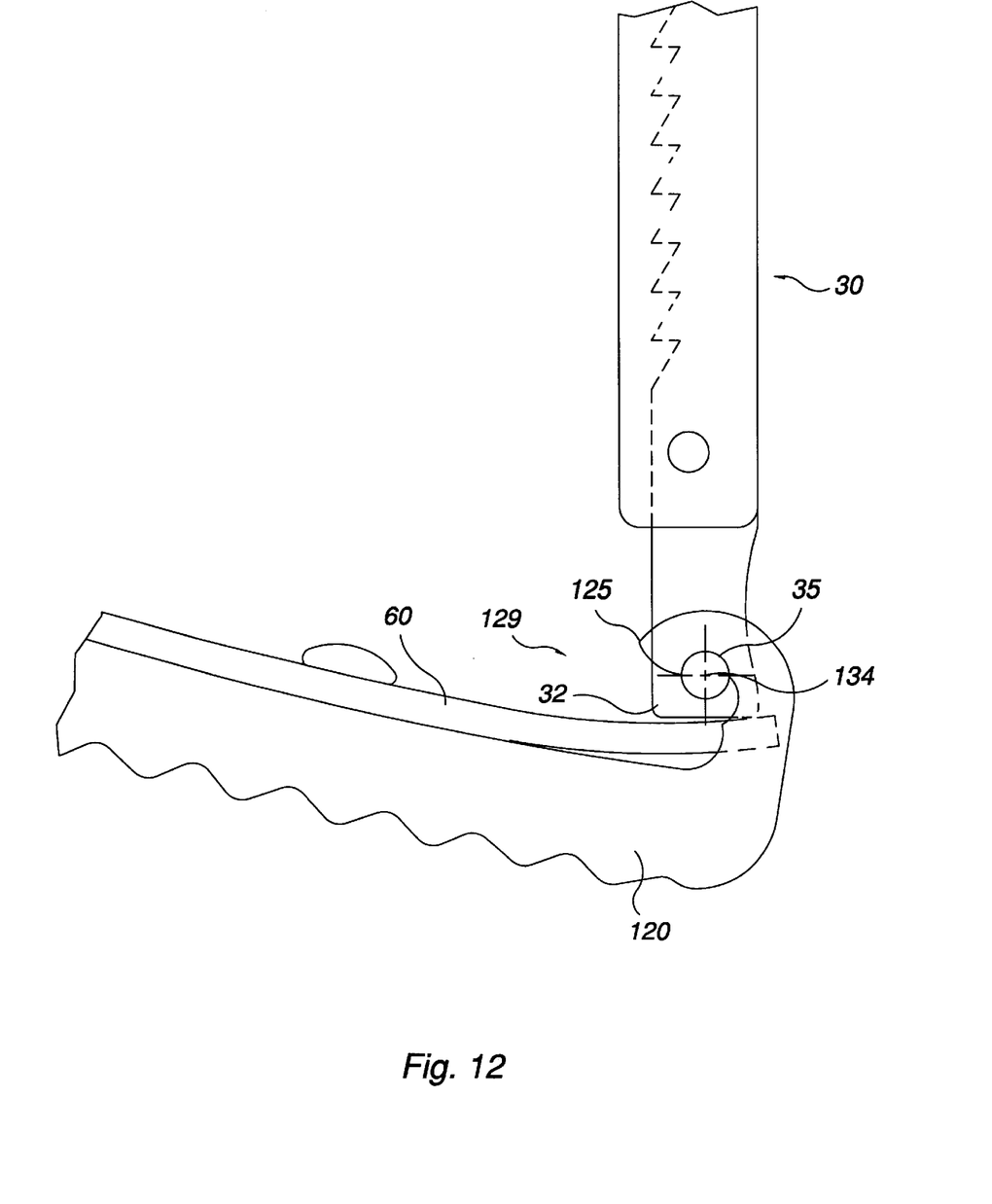
FIG. 12 is a partial side elevational view of an embodiment of the invention that has a detachable toothed bar.

In a further embodiment of the invention, the toothed bar is detachable from the pliers-shaped tool or hand held tool. In this embodiment, the toothed bar is pivotally connected at one end 32 to a handle 120 of the pliers-shaped tool or hand tool at pivot point 134, as shown in FIG. 12. End 32 of the toothed 30 bar preferably has an aperture 33, as illustrated in FIG. 2, with a rod 35 inserted through the aperture 33. The ends of rod 35 protrude from the aperture 33 on both sides of toothed bar 30. Handle 120 has clips 125 and 127 (not shown) having open slots 129 and 131 (not shown). The toothed bar 30 is clipped to the handle 120 by inserting the end 32 of bar 30 between clips 125 and 127 and snapping the ends of rod 35 into the slots 129 and 131. As illustrated in FIG. 12, the end 32 of toothed bar 30 fits between clips 125 and 127 and pivots at pivot point 134. Also, in the embodiment illustrated in FIG. 12, end 32 of bar 30 remains clipped at pivot point 134 due to a force exerted by biasing spring 60 against the end 32 of the bar 30. It will be readily apparent to those of ordinary skill in the art that there are other ways of pivotally attaching the toothed bar to the tool handle to allow the operator to remove or detach the toothed bar from the tool.

It should be readily apparent to those of ordinary skill in this field that the ratchet mechanism may be mounted on a variety of pliers-shaped tools. The hand tool illustrated in FIG. 1 is a surgical forceps which functions as a compressor. That is, the jaws of the tool normally are biased open or apart, and when the tool handles are squeezed together, the jaws of the tool come together. The ratchet mechanism may also be mounted on pliers-shaped tools that function as distractors or retractors, i.e., their jaws move apart from each other when the operator squeezes the handles. Often, retractors have scissor-like handles. Thus, when the inventive ratchet mechanism is mounted on a retractor, the mechanism is preferably located on the lever arms between the scissor-like handles and the pivot point of the tool handles.

A ratchet mechanism according to one embodiment of the invention may further be configured in the form of a kit for retrofitting a pliers-shaped tool.

In the preferred surgical embodiment, the invention is preferably fabricated of a suitably hard material such as a metal and is preferably made of stainless steel. Preferably the shield or shields are pinned or welded to the toothed bar. In an embodiment comprising two shields, for example, two plates or shields may be pinned or welded to opposite edges of the bar. FIG. 3, for example, is an exploded view of an embodiment of the invention having shields 44 and 48 that may be pinned or welded to bar 30. Because the plates extend from the bar beyond the free ends of the teeth, the row of teeth 42 is recessed between and sandwiched between the two shields or plates. The resulting width of the bar must be sufficiently narrow to slide easily through the opening in the tool handle. In an embodiment comprising two parallel rows of teeth with one shield extending therebetween, a bar with a single row of teeth may be formed first; a narrow slot is then formed along the longitudinal centerline of the teeth, and the shield is inserted in the slot and pinned or welded in place. FIG. 8 is an exploded view of a bar 130 having a slot 149 through which shield 115 is inserted.

Alternatively, the toothed bar, the row or rows of teeth and the shield or shields, may be cast or forged as a single piece. One method of forming the toothed bar is to machine it with recessed teeth as a monobloc, preferably using electrodischarge machining (EDM) according to methods known by those of ordinary skill in this field. The toothed bar may also be machined from a single block of metal using machine tools which are either manually controlled or computerized, numerically-controlled (CNC).

In operation, the inventive safety ratchet mechanism enables the operator to obtain a graduated opening or closing of the working end of the pliers-shaped tool. When the operator squeezes the handles of the tool together, the squeezing force overcomes the force of the biasing spring that biases the toothed bar toward the fixed pawl; thus, the bar slides over the pawl. As soon as the operator reduces the squeezing force, the pawl engages a ratchet tooth and locks the handles at the desired position. To unlock the handles, the operator preferably uses finger pressure to push the toothed bar from the pawl without needing to squeeze the handles together. When the teeth and pawl have sawtooth profiles, as discussed hereinabove, it is not necessary for the operator to squeeze the handles together to disengage the ratchet teeth from the pawl.

Alternatively, the teeth and pawl may be angled, if desired, using a profile that is different from a sawtooth shape. Thus, in some embodiments, to unlock the handles, the operator typically must squeeze the handles together slightly to release the pawl from the teeth and use finger pressure to push the toothed bar away from the pawl.

It should be understood that variations and modifications within the spirit and scope of the invention, beyond those discussed herein, may occur to those skilled in the art to which the invention pertains. Accordingly, all expedient modifications readily attainable by one versed in the art from the disclosure set forth herein are to be included as further embodiments of the present invention. The scope of the present invention accordingly is to be defined as set forth in the appended claims.

What is claimed is:

1. A surgical hand tool comprising:
   first and second handle portions, the second handle portion having a pawl associated therewith;
   a toothed bar having a longitudinal axis, the bar comprising first and second terminal ends, a plurality of teeth configured to engage the pawl, and at least one shield member adjacent the teeth and extending both along the direction of and transverse to the longitudinal axis of the tooth bar, the shield member having an upper edge extending along the direction of the longitudinal axis, the teeth recessed below the upper edge of the shield for protecting the hand of a tool user from cuts;
   wherein the toothed bar is pivotally attached at its first terminal end to the first handle portion and the teeth of the toothed bar are adapted to engage the pawl associated with the second handle portion.

2. The hand tool according to claim 1 wherein the first handle portion comprises a biasing spring adapted and configured to pivot the toothed bar into engagement with the pawl.

3. The hand tool according to claim 2 wherein the biasing spring comprises a leaf spring mounted to the first handle portion.

4. The hand tool according to claim 1 wherein the second handle portion has an opening and the toothed bar slides through said opening.

5. The hand tool according to claim 4 wherein the toothed bar comprises a catch to prevent the toothed bar from sliding through the opening.

6. The hand tool according to claim 1 wherein the second handle portion has a stop to prevent the toothed bar from pivoting away from the pawl.

7. The hand tool according to claim 1 wherein the toothed bar has two shield members.

8. The hand tool according to claim 1 wherein the plurality of teeth comprises two rows of teeth and wherein the at least one shield member is located between said two rows of teeth.

9. The hand tool according to claim 8, further comprising two additional shield members, wherein the two rows of teeth are located between the two additional shield members.

10. The hand tool according to claim 8 wherein the two rows of teeth have two exposed lateral edges, said exposed lateral edges being tapered toward the at least one shield member.

11. The hand tool according to claim 1 wherein the toothed bar is releasably attached at its first terminal end to the first handle portion.

12. The hand tool according to claim 1 wherein the toothed bar is machined.

13. The hand tool according to claim 1 wherein the teeth and pawl are arranged as corresponding sawtooth serrations.

14. A ratchet mechanism for preventing undesired relative movement of two handle portions of a surgical hand tool comprising:
    a toothed bar having a longitudinal axis, the bar comprising a first end adapted and configured to be pivotally connected to at least one handle portion and a second end adapted and configured to move relative to the other handle portion when the handle portions undergo relative movement, the toothed bar having a plurality of teeth designed and configured to interact with a pawl on the hand tool, and at least one shield member adjacent the toothed bar and extending both along the direction of and transverse to the longitudinal axis of the tooth bar, the shield member having an upper edge extending along the direction of the longitudinal axis, the teeth recessed below the upper edge of the shield for protecting the hand of a tool user from cuts.

15. The ratchet mechanism according to claim 14 wherein the other handle portion has an opening and the toothed bar slides through said opening.

16. The ratchet mechanism according to claim 15 wherein the toothed bar comprises a catch to prevent the toothed bar from sliding through the opening.

17. The ratchet mechanism according to claim 16 wherein the first end of the toothed bar is designed and configured to receive a biasing force to pivot the toothed bar into engagement with the pawl.

18. The ratchet mechanism according to claim 17 wherein the first end of the toothed bar is designed and configured to interact with a free end of a leaf spring mounted to the handle portion of the hand tool.

19. The ratchet mechanism according to claim 14 wherein the toothed bar has two shield members.

20. The ratchet mechanism according to claim 14 wherein the plurality of teeth comprises two rows of teeth and wherein the at least one shield member is located between said two rows of teeth.

21. The ratchet mechanism according to claim 20, further comprising two additional shield members, wherein the two rows of teeth are located between the two additional shield members.

22. The ratchet mechanism according to claim 20 wherein the two rows of teeth have two exposed lateral edges, said exposed lateral edges being tapered toward the at least one shield member.

23. The ratchet mechanism according to claim 14 wherein the first end of the toothed bar is detachable from the at least one handle portion.

24. The ratchet mechanism according to claim 14 wherein the toothed bar is machined.

25. The ratchet mechanism according to claim 14 wherein the toothed bar is designed and configured to prevent the handle portions from separating unless the operator disengages the teeth from the pawl.

26. The ratchet mechanism according to claim 14 wherein the teeth are arranged as sawtooth serrations.

27. A surgical hand held tool comprising:

a first extending member;

a second extending member having an opening associated therewith and a pawl;

a working end movable by relative movement of the extending members;

a toothed bar having a longitudinal axis, the bar having a first end pivotally connected to the first extending member and a second end adapted and configured to move through the opening in the second extending member, the toothed bar having teeth adapted and configured to engage with the pawl, and at least one shield member adjacent the teeth and extending both along the direction of and transverse to the longitudinal axis of the tooth bar, the shield member having an upper edge extending along the direction of the longitudinal axis, the teeth recessed below the upper edge of the shield for protecting the hand of a tool user from cuts; and a biasing member to urge the teeth into engagement with the pawl;

wherein the toothed bar and second extending members are designed and configured so that the toothed bar does not become disassociated from the second extending member.

28. The hand held tool according to claim 27, configured and adapted so that the first and second extending members can be moved relative to each other in both directions by use of one hand of the operator.

29. The hand held tool according to claim 27 wherein the toothed bar has a longitudinal axis between the first end and the second end and wherein the teeth and pawl are configured to have contact surfaces that are substantially perpendicular to the longitudinal axis of the toothed bar.

30. The hand held tool according to claim 27 wherein the toothed bar is curved.

31. The hand held tool according to claim 27 wherein the opening has a stop to prevent the toothed bar from being disassociated with the second extending member.

32. The hand held tool according to claim 31 wherein the stop prevents the toothed bar from pivoting away from the second extending member.

33. The hand held tool according to claim 27 wherein the toothed bar has a catch to prevent the toothed bar from sliding through the opening.

34. The hand held tool according to claim 33 wherein the opening has a U-shape having an open back.

35. The hand held tool according to claim 27 wherein the biasing member is a leaf spring associated with the first extending member, and further comprising a pivotal connection wherein the leaf spring biases the toothed bar to rotate about the pivotal connection.

36. The hand held tool according to claim 27 wherein the biasing member engages the toothed bar and the second extending member.

37. A surgical hand tool comprising:

a first extending member;

a second extending member having an opening associated therewith and a pawl;

a working end movable by relative movement of the extending members for performing a surgical procedure;

a toothed bar having a longitudinal axis, the bar having a first end pivotally connected to the first extending member and a second end, the toothed bar having teeth adapted and configured to engage with the pawl, and at least one shield member adjacent the teeth and extending both along the direction of and transverse to the longitudinal axis of the tooth bar, the shield member having an upper edge extending along the direction of the longitudinal axis, the teeth recessed below the upper edge of the shield for protecting the hand of a tool user from cuts, wherein at least a portion of the edge extends beyond the free ends of the teeth.

* * * * *